(12) United States Patent
Noo et al.

(10) Patent No.: US 8,306,304 B2
(45) Date of Patent: Nov. 6, 2012

(54) PRECISE IMAGE RECONSTRUCTION OF SPIRAL CT IMAGES AT OPTIONAL PITCH VALUES

(75) Inventors: Frédéric Noo, Midvale, UT (US); Harald Schöndube, Erlangen (DE); Karl Stierstorfer, Erlangen (DE)

(73) Assignees: Siemens Aktiengesellschaft, Munich (DE); University of Utah Research Foundation, Salt Lake City, UT (US)

( * ) Notice: Subject to any disclaimer, the term of this patent is extended or adjusted under 35 U.S.C. 154(b) by 670 days.

(21) Appl. No.: 12/462,000

(22) Filed: Aug. 31, 2009

(65) Prior Publication Data

US 2011/0052021 A1 Mar. 3, 2011

(51) Int. Cl.
*A61B 6/03* (2006.01)
(52) U.S. Cl. .......................................... 382/131; 378/15
(58) Field of Classification Search .............. 378/4, 15, 378/210, 901; 382/128–132
See application file for complete search history.

(56) References Cited

U.S. PATENT DOCUMENTS

2004/0125910 A1* 7/2004 Katsevich ................. 378/15
2006/0291611 A1* 12/2006 Pack et al. .................. 378/4

OTHER PUBLICATIONS

Schondube et al., Towards an Efficient Two-Step Hilbert Algorithm for Helical Cone-Beam CT, Jul. 2007, 9th International Meeting on Fully Three-Dimensional Image reconstruction in Radiology and Medicine, pp. 120-123.*
Danielsson et al., Toward Exact 3D-reconstruction for Helical Cone-Beam scanning of Long Objects. A new Detector Arrangement and a New Completeness Condition, 1997, International Meeting on Fully Three-dimensional Image Reconstruction in Radiology and Nuclear Medicine, pp. 141-144.*
A. Katsevich, vol. 47, pp. 2583-2597 Analysis of an exact inversion algorithm for spiral cone-beam CT Phys. Med. Biol., 2002; Others; 2002.
Y. Zou et. al. Exact image reconstruction on PI-lines from minimum data in helical cone-beam CT Phys. Med. Biol., vol. 49, pp. 941-959, 2004; Others; 2004.
J. Pack et al., Cone-Beam Reconstruction Using the Backprojection of Locally Filtered Projections, IEEE Med. Imag. vol. 24, No. 1, pp. 70-85, 2005; Others; 2005.

(Continued)

*Primary Examiner* — Toan Ton
*Assistant Examiner* — John Corbett
(74) *Attorney, Agent, or Firm* — Harness, Dickey & Pierce, P.L.C.

(57) ABSTRACT

At least one embodiment of the invention relates to a method for the reconstruction of image data of an examined object from measuring data, wherein the measuring data were detected by a detector within and outside of its Tam-Danielsson window during a relative spiral movement between a radiation source of a computer tomography system and the examined object. As a result of the spiral movement, the measuring data outside of the Tam-Danielsson contain interruptions. A mathematically precise first reconstruction of first image data is realized in at least one embodiment based on the measuring data by using only measuring data from the Tam-Danielsson window. A mathematically precise second reconstruction is furthermore realized of second image data from the measuring data in at least one embodiment, using at least among other things measuring data from outside of the Tam-Danielsson window, wherein the interruption of the measuring data is compensated for by using existing measuring data and/or the first image data and/or other image data obtained from existing measuring data. Finally, the first image data and the second image data are combined.

29 Claims, 8 Drawing Sheets

OTHER PUBLICATIONS

P. Danielsson et al. in Proc., pp. 141-144; Meeting on Fully 3D Image Reconstruction in Radiology and Nuclear Medicine (Pittsburgh, PA), D. Townsend et al. Eds., 1997; Others; 1997; US.

C. Bontus et al. A quasiexact reconstruction algorithm for helical CT using a 3-Pi acquisiton Med. Phys., vol. 30, No. 9, pp. 2493-2502, 2003; Others; 2003.

A. Katsevich, On two versions of a 3 algorithm for spiral CT Phys. Med. Biol., vol. 49, No. 11, pp. 2129-2143, 2004; Others; 2004.

C. Bontus et al. EnPiT: Filtered Back-Projection Algorithm for helical CT Using an n-Pi Acquisition IEEE Transaction Med. Imag. vol. 24, No. 8, pp. 977-986, 2005,; Others; 2005.

A. Katsevich 3PI Algorithms for helical computer tomography Advances in Applied Mathematics, vol. 36, pp. 213-250, 2006; Others; 2006.

R. Proska et al. The n-PI-Method for Helical Cone-Beam CT IEEE Trans. Med. Imag., vol. 19, No. 9, pp. 848-863, 2000; Others; 2000.

D. Heuscher et al. Redundant data and exact helical cone-bema reconstruction Phys. med. Biol., vol. 49, pp. 2219-2238, 2004; Others; 2004.

T. Köhler et al. The Radon-Split Method for Helical Cone-Beam CT and its Application to Nongated Reconstruction IEEE Trans. Med. Imag., vol. 25, No. 7, pp. 882-897, 2006; Others; 2006.

A. Zanyatin et al. Helical CT Reconstruction with Large Cone Angle IEEE Nuclear Science Symposium Conference Record, vol. 4, pp. 2264-2267, 2006; Others; 2006.

A. Katsevich et al, Beekman et al. Optimized reconstruction alogorithm for helical CT with fractional pitch between 1PI and 3PI Meeting on Fully 3D Image Reconstruction in Radiology and Nuclear Medicine, pp. 333-336, 2007; Others; 2007; DE.

Stierstorfer et al. Weighted FBP—a simple approximate 3D FBP algorithm for multislice spiral CT with good dose usage for arbitrary pitch Phys. Med. Bio. vol. 49, pp. 2209-2218, 2004; Others; 2004.

H. Kudo et al. Exact and approcimate algorithms for helical cone-beam CT Phys. Med. Biol. vol. 49, No. 13, pp. 2913-2931, 2004; Others; 2004.

G. Shechter et al. The fequency split method for helical cone-beam reconstruction Med. Phys., vol. 31, No. 8, pp. 2230-2236, 2004; Others; 2004.

X. Tang et al., Handling dara redundancy in helical cone beam reconstruction with a cone-angle-based window function and its asymptotic approximation Med. Phys., vol. 34, No. 6, pp. 1989-1998, 2007; Others; 2007.

H. Schöndube et al. F. Beekman et al. Towards an Efficient Two-Step Hilbert Algorithm for Helical Cone-Beam CT Meeting on Fully 3D Image Reconstruction in Radiology and Nuclear Medicine, pp. 120-123, 2007; Others; 2007; DE.

IEEE Nuclear Science Symposium Conference Record NSS '07, Comparative evaluation of two analytical methods for Helical Cone-Beam Tomography vol. 6, pp. 4467-4471, 2007 H. Schöndube, K. Stierstorfer, F. Dennerlein; Others; 2007.

Claas Bontus and Thomas Koehler; Reconstruction Algorithms for Computed Tomography; Advances in Imaging and Electron Physics, vol. 151; Book; 63 pages.

Harald Schöndube, Karl Stierstorfer, Federic Noo; "Accurate helical cone-beam CT reconstruction with redundant data", 2009 Institute of Physics and Engineering in Medicine, Phys. Med.Biol.54 (2009) 4625-4644.; Book; 2009.

H. Kunze, "Iterative Rekonstruktion in der Medizinischen Bildverarbeitung", Ph. D. dissertation, Friedrich-Alexander-Universität Erlangen_Nürnberg, Germany 2007.

K. Tam, S. Samarasekera, and F. Sauer, "Exact cone-beam CT with a spiral scan", Phys. Med. Biol., vol. 43, pp. 1015-1024, 1998.

* cited by examiner

PRECISE IMAGE RECONSTRUCTION OF SPIRAL CT IMAGES AT OPTIONAL PITCH VALUES

FIELD

At least one embodiment of the invention generally relates to a method for reconstructing image data of an examined object by using measuring data, wherein these data were detected by a detector during a relative spiral movement between a radiation source for a computer tomography system and an examined object.

BACKGROUND

Methods for scanning an examined object with a CT system are generally known, wherein circular scans, sequential circular scans with forward-feed motion, or spiral scans can be used. These scans are designed to record absorption data of the examined object from different angles, which are recorded with the aid of at least one X-ray source and at least one opposite-arranged detector. The collected projection data are then converted with the aid of corresponding reconstruction methods to obtain sectional or volume images through the examined object.

A so-called filtered back projection process (FBP) is used nowadays as standard method for the reconstruction of computer tomography images from X-ray CT data sets of a CT device, for which during the data acquisition an X-ray source emitting cone-shaped X rays moves along a helical path around the object to be detected and/or the volume of interest (VoI). This method functions quite well in principle but is an approximation method, meaning that mathematically precise reconstructions are not possible, thereby resulting in artifacts. Problems with the so-called cone beam artifacts occur in particular when using the FBP method because it is an approximation method. These artifacts furthermore increase along with an increase in the number of detector lines, which is particularly serious if the number of detector lines increases noticeably, for example exceeds 100, as can be the case with the newest types of detectors.

Attempts have therefore been made to develop methods, which permit a mathematically precise and stable reconstruction. The "differentiated back projection" along so-called "n lines" is one example of such an attempt. Referred to as n lines are in particular those lines which twice intersect the helical path at a distance of less than one complete rotation. The resulting back projection data correspond to the Hilbert transform of the desired image data, so that the desired image data can subsequently be computed with a following inverse Hilbert transformation. The method for a three-dimensional differentiated back projection with subsequent inverse Hilbert transformation is described in further detail in the publication by H. Schondube, K. Stierstorfer, F. Dennerlein, T. White and F. Noo: "Towards an efficient two-step Hilbert algorithm for helical cone-beam CT." in Proc. 2007 Meeting on Fully 3D Image Reconstruction in Radiology and Nuclear Medicine (Lindau, Germany), F. Beckman and M. Kachelriess, Edition 2007, pp 120-123, the entire contents of which are hereby incorporated herein by reference. Since this method is mathematically accurate and no artifacts can occur because of the fan geometry of the X-ray beam, it can be used to reconstruct good images even if the number of detector lines increases strongly, as described in the above.

However, this reconstruction method is restricted to the use of measuring data from the detector which are located within the so-called Tam-Danielsson window (henceforth called "TD window") on the detector. This TD window is defined by the projection onto the detector of the X-ray source trajectory, meaning the helical path of the X-ray source. Data measured in the detector regions outside of this TD window cannot be used with the aforementioned method. However, since the conical beam from the X-ray source of standard CT systems is formed such that it hits the complete detector, meaning also the regions outside of the TD window, some amounts of the radiation dose remain unused. To be sure, it would theoretically be possible to design the X-ray source such that it can generate an X-ray beam that impinges precisely on the TD window. However, this would result in no flexibility for adjusting the pitch height of the helical curve, meaning the pitch, and would otherwise be extremely costly so that it makes more sense to use a rectangular standard detector with a traditional X-ray source.

However, it is desirable to be able to use data outside of the TD window. In contrast to data measured inside the TD window, the data measured outside of this window are redundant and are not required for a complete reconstruction. These redundant data can be used to reduce the image noise while maintaining the same image resolution.

Approximation methods can in principle be used for utilizing redundant data, wherein again the advantage of the above-described mathematically precise reconstruction is lost. The publication by J. Pack, F. Noo and R. Clackdoyle: "Cone-beam reconstruction using the back projection of locally filtered projections," IEEE Trans. Med. Imag., Vol. 24, No. 1, pp 70-85, January 2005, describes an approach for a mathematically precise reconstruction that also allows using detector data measured outside of the TD window. However, this method is limited to realizing a differentiated back projection and a subsequent inverse Hilbert transformation for each individual voxel, wherein multiple reconstructions are respectively used for the individual voxels, which then requires an averaging of the reconstruction values of the individual voxels. This results in considerable computation expenditure for reconstructing a complete volume of interest, making this method very inefficient and unusable in everyday practice.

SUMMARY

At least one embodiment of the present invention provides an efficient, but nevertheless mathematically precise method for the reconstruction of CT images. At least one embodiment of the invention furthermore provides a corresponding control and computer unit, a CT system, a computer program and a computer program product.

At least one embodiment of the invention is directed to a method, as well as a control and computer unit, a CT system, a computer program and a computer program product.

The method according to at least one embodiment of the invention is used for reconstructing image data of an examined object by using measuring data previously recorded by a detector within and outside of a Tam-Danielsson window during a relative spiral movement between a radiation source of a computer tomography system and the object to be examined. As a result of the spiral movement, interruptions occur in the data measured outside of the Tam-Danielsson window. A mathematically precise first reconstruction of first image data is realized by using only measuring data from the Tam-Danielsson window. A mathematically precise second reconstruction of second image data is carried out, which also uses at least some data measured outside of the Tam-Danielsson window. For the second reconstruction, the interruption in the measuring data are compensated for by using available measuring data and/or first image data and/or other reconstructed image data from available measuring data. Finally, the first image data and the second image data are then combined.

The Tam-Danielsson window represents a defined, precisely delimited and cohesive region on the surface of the detector. The boundaries of the Tam-Danielsson window are fixed by selecting the pitch factor, which is the same as selecting the course of the spiral path of the X-ray source relative to the object to be examined.

The measuring data used for the image reconstruction are such that outside of the Tam-Danielsson window an interruption occurs, which corresponds to the interrupted illumination of the examined object at specific pitch values. If an interruption in the illumination is present, it means that the projection of a volume element of the examined object enters the detector at a specific angle position of the X-ray source along the spiral path, so as to exit again at a later instant during the course of the spiral path and then enter again at an even later instant. No measuring data for this volume element consequently exists between the exit and the reentry.

This effect of the interrupted illumination does not exist between the entry of the projection for a volume element into the Tam-Danielsson window and the exit from the Tam-Danielsson window. The first reconstruction for which exclusively measuring data from the Tam-Danielsson window are used can therefore be computed without problems.

The situation is different for the second reconstruction, which uses exclusively or at least in part measuring data that were recorded by detector elements outside of the Tam-Danielsson window, which means that the available measuring data can therefore also have gaps and/or interruptions. To be able to realize an image reconstruction, this interruption is compensated for, wherein a complete compensation can be realized. In that case, a replacement is procured for each date that is missing due to the interruption or a necessary replacement variable is produced for the reconstruction. However, a partial compensation can also be used, which is advantageous if not all measuring data missing due to the interruption are required for the image reconstruction.

Two sets of image data are therefore available following the first and the second image reconstruction. The two sets of image data are then combined to increase the quality of the resulting image, in particular to avoid any image noise.

There are several different steps for compensating the measuring data that are missing due to the interruptions. These steps are based on using existing measuring data, the previously reconstructed first image data, or other image data, wherein the other image data can be image data obtained by using those available data which are also utilized for reconstructing the second image data. A mathematically precise reconstruction or an approximation method can be used to obtain these other image data. The latter has the advantage that approximate image reconstruction methods are less affected by the gaps in the available measuring data than the mathematically precise reconstructions. An approximate image reconstruction could therefore be realized, which does not require the data missing because of the gaps. This could be followed by determining from the image data, obtained by approximation from the missing data, which data could be used for the mathematically precise reconstruction.

A combination of the aforementioned three compensation methods is furthermore possible, wherein especially advantageous options for the compensation are listed in the following:

First, available measuring data can be used by utilizing an interpolation or extrapolation of the present measuring data on the interruptions, upon which the mathematically precise second reconstruction is based. The missing measuring data are thus replaced with values determined from the existing measuring data. In the simplest case, the values of the closest detected measuring data can simply be inserted for the missing measuring data.

Second, the first image data can be used to compute projection data that correspond to the interruptions, wherein these data are used as basis for the mathematically precise second reconstruction. If we know the weakening distribution of the examined object, it is possible to compute which measuring data must be obtained during a CT scan. A physical model of the CT measurement is used for computing this projection data.

Third, the first image data can be used by computing Hilbert transformations from the first image data, which are then used for the mathematically precise second reconstruction. These steps are particularly advantageous if the second image reconstruction is based on the computation of inverse Hilbert transformations.

According to one modification of at least one embodiment of the invention, a mathematically precise third reconstruction of third image data is realized by using among other things measuring data from outside of the Tam-Danielsson window, wherein the interruption of the data are compensated for by using available measuring data and/or the first image data. Following this, the first image data, the second image data and the third image data are combined. The determination of the third image data, including the compensation of the interruptions, preferably occurs in the same way as that for the second image data, wherein it is advantageous to use for the third image reconstruction a different area for measuring the data on the detector surface than for the second image reconstruction. Of course, these steps can also be used for a fourth, fifth, sixth etc. mathematically precise reconstruction of third image data.

Combining the image data, meaning the first image data, the second image data and if applicable also the third image data by forming an average value is particularly simple and efficient, wherein the averaging is preferably realized pixel-by-pixel.

According to a different modification of at least one embodiment of the invention, the image reconstructions, meaning the first, second and if applicable also the third reconstruction, are volume-based reconstructions achieved with the aid of differentiated back projections and subsequent inverse Hilbert transformations. The volume-based image reconstruction must be distinguished from the pixel-by-pixel image reconstruction for which separate image values are computed for each volume element of the volume of interest. With the volume-based image reconstruction, the computation takes place simultaneously for a complete volume or at least successively for a plurality of areas.

The volume-based reconstruction for the first image data preferably is obtained with the aid of differentiated back projections via a first group of surfaces formed with M-lines, those for the second image data with the aid of differentiated back projections via a second group of surfaces formed with M-lines, and if applicable those for the third image data with the aid of differentiated back projections via a third group of surfaces formed with M-lines. The M-line herein is a line that connects a specific position of the X-ray source along its spiral trajectory to a specific point on the detector surface. For each of the two or three image reconstructions, a group of surfaces is therefore defined, wherein each surface is spanned by a number of M lines. These groups are advantageously embodied such that they do not have joint surfaces, meaning there is no surface that belongs to two or three groups. Each group of surfaces is advantageously embodied to cover the volume of interest of the examined object. That is to say, that if all surfaces of a group are "stacked," the resulting stack covers the total volume of interest. The volume of interest in this case is the region on the examined object, which is to be shown with the image data.

For an embodiment according to the invention, each surface formed by the respective M lines of the first group completely impinges on the detector within the Tam-Danielsson window, while for the second group the surface formed by the respective M lines impinges above or below the Tam-Danielsson window and, if a third group is used, each surface formed by the respective M lines impinges on the detector above or below the Tam-Danielsson window. If the second and the third group are used, it is advantageous if the second group impinges above and the third group impinges below the Tam-Danielsson window, or vice versa, resulting in a complete use of the detector surface.

According to one embodiment of the invention, all M lines within one group impinge on the same detector line. Thus, a specific detector line exists for the first group, which all M-line surfaces of the first group intersect. The same correspondingly applies to the second and if applicable also the third group. It is therefore advantageous if there are differences between the detector lines for the first group, the second group and if applicable also the third group, wherein this also results in the efficient use of the total detector surface.

It is advantageous if all M lines that form a surface are parallel when projected onto a plane that is perpendicular to the longitudinal axis of the spiral movement. It is furthermore also advantageous if data are interpolated between the measuring data, so that the M lines of a surface are equidistant. Since the measuring data are not continuous, but are detected at discrete measuring instances by discrete detector elements, the M lines that can be generated based on the existing measuring data are normally not equidistant. This can be taken into account with an interpolation. The same correspondingly applies to the parallel arrangement of the M lines of a surface.

For an embodiment of the invention, the image data reconstructed for the different reconstructions are transformed into Cartesian coordinates and all image data are then combined within this coordinate system.

It is particularly advantageous if the spiral movement is selected such that the dimensions of the Tam-Danielsson window during the detection of the data are smaller than the dimensions of the Tam-Danielsson window where it meets the outside edges of the two outermost detector lines. The reduction of the Tam-Danielsson window as compared to the maximum size can be achieved through a reduction in the pitch value, corresponding to the increase in the redundancy of the measuring data. This goes hand in hand with the increase in the effect of the interrupted lighting. The interrupted lighting typically exists for all pitch values that are lower than a specific threshold value. This threshold value depends on the diameter of the volume of interest, wherein typical threshold values are in the range of a pitch factor between 0.75 and 1.35. The present invention is particularly suitable for the reconstruction of CT images for the CT scanning with small pitch values, especially for pitch values lower than the aforementioned threshold value.

The control and computer unit according to at least one embodiment of the invention is used for the reconstruction of image data of an examined object from measuring data supplied by a CT system. It comprises a program memory for storing program code, wherein program code is made available—if applicable—which is suitable for implementing a method as described in the above. The CT system according to the invention comprises a control and computer unit of this type. It can furthermore comprise other components, e.g. components that are required for detecting measuring data.

The computer program according to at least one embodiment of the invention comprises program code segments suitable for realizing at least one embodiment of the aforementioned method if the computer program is run on a computer.

The computer program product comprises program code segments stored on a computer-readable data carrier, which are suitable for implementing the aforementioned method if the computer program is run on a computer.

BRIEF DESCRIPTION OF THE DRAWINGS

The invention is described in further detail in the following with the aid of an example embodiment, showing in.

DETAILED DESCRIPTION OF THE EXAMPLE EMBODIMENTS

Figure 1:
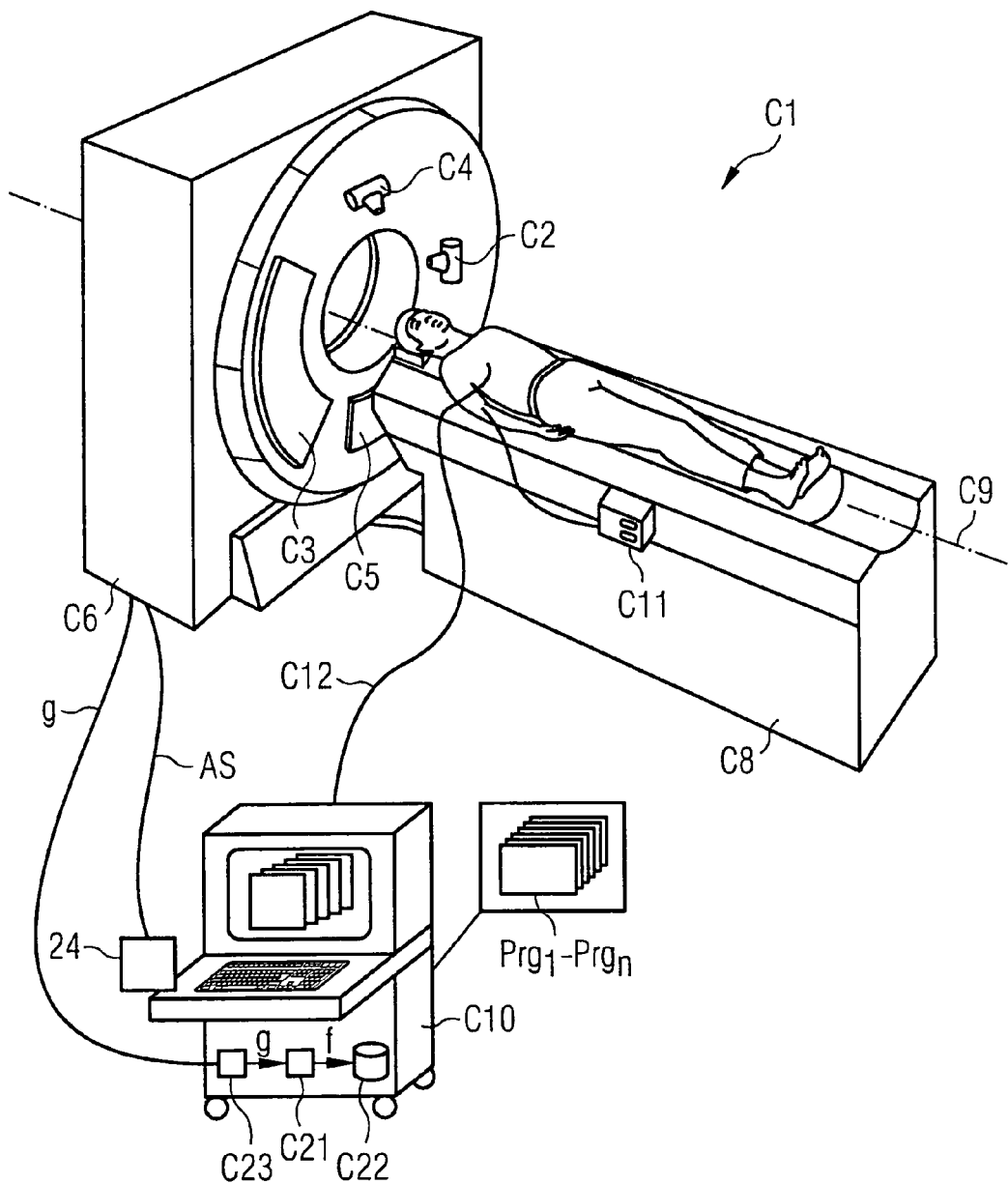
FIG. 1 A first schematic representation of an example embodiment of a computer tomography system with an image reconstruction component.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 schematically illustrates a first computer tomography system C1 with an image reconstruction device C21. Located in the gantry housing C6 is an enclosed gantry, not shown herein is, with thereon arranged first X-ray tube C2 and opposite positioned detector C3. A second X-ray tube C4 with opposite positioned detector C5 can optionally be arranged in the CT system shown herein, so that a higher time resolution can be achieved with the additionally provided radiator/detector combination or such that "dual energy" examinations can be carried out when using different X-ray energy spectra in the radiator/detector systems.

The CT system C1 furthermore comprises a patient stretcher C8, designed for pushing the patient during the examination into the measuring field along a system axis C9, which is also called the z-axis. In the process, the X-ray source C2 and/or C4 respectively rotates around the patient. Parallel thereto, the opposite-arranged detector C3 and/or C5 also rotates along with the X-ray source C2 and/or C4 to detect the projection measuring data, which are then used for the reconstruction of sectional images. A spiral scan is realized by pushing the patient for the rotational scanning with the X rays continuously along the system axis C9, through the examination field between the X-ray tube C2 and/or C4 and the detector C3 and/or C5. As a result of the movement of the patient along the axis C9 and the simultaneous rotation of the X-ray source C2 and/or C4, a helical path is followed during the measuring operation with a spiral scan for the X-ray source C2 and/or C4. This same path can also be achieved by moving the gantry along the axis C9 while the patient remains stationary.

The CT system C1 is controlled by a computer and control unit C10 with the aid of a program code Prg1 to Prgn stored in a memory. Acquisition control signals AS can be transmitted from the control and computer unit C10 via a control interface 24 to activate the CT system C1 in accordance with specific measuring protocols.

The projection measuring data g (henceforth call raw data) acquired by the detector C3 and/or C5 are transmitted via a raw data interface C23 to the control and computer unit C10. These raw data g are subsequently processed further in an image reconstruction component C21, if applicable following a suitable pre-processing. The image reconstruction component C21 for this exemplary embodiment is realized in the control and computer unit C10 in the form of software on a processor, e.g. in the form of several computer program codes Prg1 to Prgn. The image data f reconstructed by the image reconstruction component C21 are then stored in a memory C22 of the control and computer unit C10 and/or are displayed in the known manner on the monitor of the control and computer unit C10. The image data can furthermore be fed via an interface, not shown in FIG. 1, into a network connected to the computer tomography system C1, for example to a radiological information system (RIS), and can be stored there in an accessible mass storage unit or can be displayed as images.

The control and computer unit C10 can additionally also realize the function of an EKG or ECG, wherein a line C12 for diverting the ECG potentials is used between the patient and the control and computer unit C10. The CT system C1 shown in FIG. 1 additionally also comprises a contrasting means C11 injection device, used to inject additional contrasting means into the patient's circulation, so that the patient's blood vessels, in particular the chambers of the beating heart, can be displayed better. The option furthermore exists of realizing perfusion measurements, for which the proposed method is also suitable.

Figure 2:
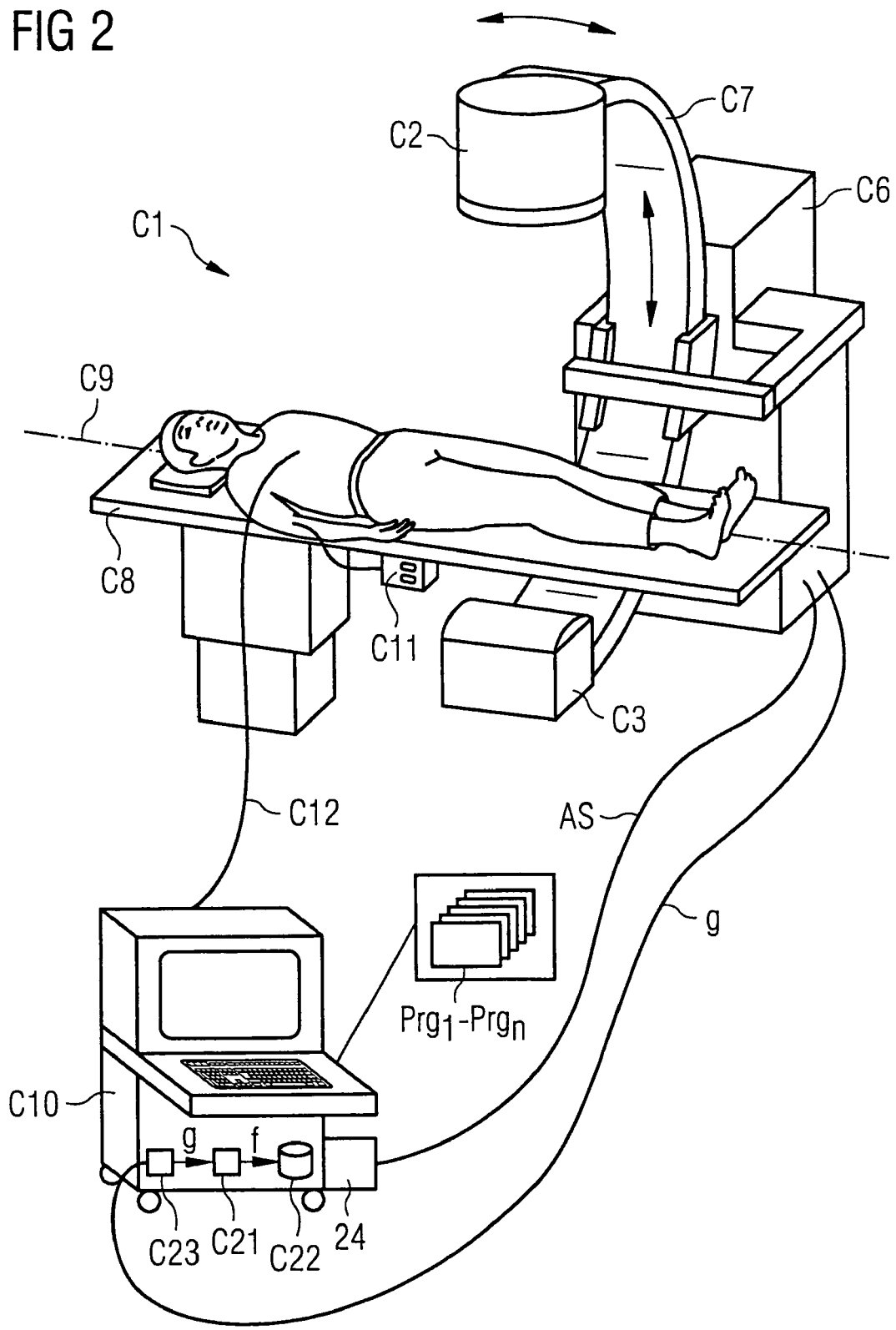
FIG. 2 A second schematic representation of an example embodiment of a computer tomography system with an image reconstruction component.

FIG. 2 shows a C-bend system which, in contrast to the CT system shown in FIG. 1, is provided with the C-bend C7 on the housing C6 with thereto attached X-ray tube C2 on one side and the detector C3 that is attached on the opposite side. The C-bend C7 is also pivoted around a system axis C9, thereby allowing a scanning from a plurality of scanning angles, so that corresponding projection data g can be obtained from a plurality of projection angles. In the same way as the CT system shown in FIG. 1, the C-bend system C1 in FIG. 2 is also provided with a control and computer unit C10 of the type as described for FIG. 1.

An embodiment of the invention can be used in both the systems shown in FIG. 1 and FIG. 2 and can furthermore in principle also be used for other CT systems, e.g. for CT systems with a detector forming a complete ring. It is essential for the explanations provided in the following that a helical scan can be realized.

The data acquisition geometry and the other terms used herein are explained in the following with the aid of FIG. 3. The three-dimensional density distribution or weakening distribution to be reconstructed is referred to as f(x), wherein x=(x, y, z) is a vector in the Cartesian coordinate system. It is assumed that this Cartesian coordinate system (x, y, z) is immobile, relative to the object to be examined, and that the z axis corresponds to the direction in which the examined object is moved during a rotation of the X-ray source, relative to the CT device, meaning the z axis in the final analysis is the system axis for the forward movement along the helical path (in the direction of positive z values).

The movement of the X-ray source relative to the examined object on the helical path can be expressed as follows:

$$a(\lambda)=[Ro\ cos(\lambda+\lambda o), Ro\ sin(\lambda+\lambda o), zo+h\lambda] \quad (1)$$

Ro in this case represents the radius of the spiral movement of the X-ray source and 2πh indicates the pitch height of the helix. λ is a free variable that describes the position of the X-ray source on the helical path. The position of the X-ray source can thus be provided with the value of λ, wherein λo and λo correspond to the coordinates of the X-ray source at a starting point.

In the following, we assume that a standard, rectangular, cylinder-segment shaped detector Det is used, such as the one shown schematically in FIG. 3. A detector Det of this type has Nrows of detector lines with respectively Ncols of detector elements, which jointly form a cylinder segment with a radius D around the cone tip, meaning the X-ray source. Three orthogonal unit vectors that rotate around the z axis with the variable X can be used for the mathematical description of the position on the detector Det, meaning the position of the detector elements relative to the object:

$$eu(\lambda)=[-sin(\lambda+\lambda o),\ cosin(\lambda+\lambda o),0] \quad (2)$$

$$ev(\lambda)=[-cosin(\lambda+\lambda o),-sin(\lambda+\lambda o),0] \quad (3)$$

$$ew=[0,0,1] \quad (4)$$

These elements are arranged such that ev is parallel to the (x, y) plane and that the direction of a line is defined from the cone tip to the detector Det that intersects the z axis. The point of intersection between this straight line and the detector Det simultaneously also defines the origin of the detector coordinates. The other directions of the detector coordinates are then defined by ew, which is parallel to the z axis, and eu which is defined such that the three unit vectors eu, ev, ew form the ortho normal base of a three-dimensional space R3. As a result of the selected detector geometry, projections of the detector lines onto the eu/ew plane are parallel to eu.

Measuring values are recorded on the detector Det by the individual detector pixels with equidistant detector coordinates w and γ. The coordinate w represents the detector line and is counted in the direction of the dimension ew whereas γ defines the fan angle of the detector gap, meaning the angle between two planes, one of which contains the cone tip and the z axis while the other plane contains the cone tip and the respective detector gap. Positive values of the coordinate γ correspond to the positive direction of the unit vector eu in the detector coordinate system.

With a geometry defined in this way, the measuring of the detected data g can be described as follows:

$$g(\lambda, \gamma, w) = \int_o^\infty f(a(\lambda) + t\alpha(\lambda, \gamma, w))dt \quad (5)$$

Wherein α(λ,γ,w) describes a unit vector, which points from a(λ) to a detector element on the fan angle γ and shows w in the detector line, meaning:

$$\alpha(\lambda, \gamma, w) = \frac{(D\sin\gamma e_v(\lambda) + D\cos\gamma e_v(\lambda) + we_w)}{\sqrt{D^2 + w^2}} \quad (6)$$

During the data acquisition, a line integral is thus formed via the weakening distribution f of the examined object along a line from the X-ray source to the detector pixel with the coordinates γ and w.

The Tam-Danielsson window (TD window) forms the region within the detector Det, inside of which the data necessary and sufficient for a precise reconstruction are detected. This corresponds to a detection of data from a projection angle range of 180° for each voxel of the volume of interest. The indicated range means that from the view of the respective voxel, this voxel is irradiated by the X-ray source from different positions over a range of 180° and that the radiation reaches the detector (Det.). Conversely, the data detected by the detector pixels outside of the TD window are redundant data and are not necessary for the precise reconstruction.

For the geometry shown in FIG. 3, the upper limit wtop and the lower limit wbottom of the TD window can be described as follows:

$$wtop = \frac{Dh\pi/2 - \gamma}{R_o \cos\gamma}, wbottom = \frac{Dh\pi \cdot 2 + \gamma}{R_o \cos\gamma} \quad (7)$$

Figure 3:
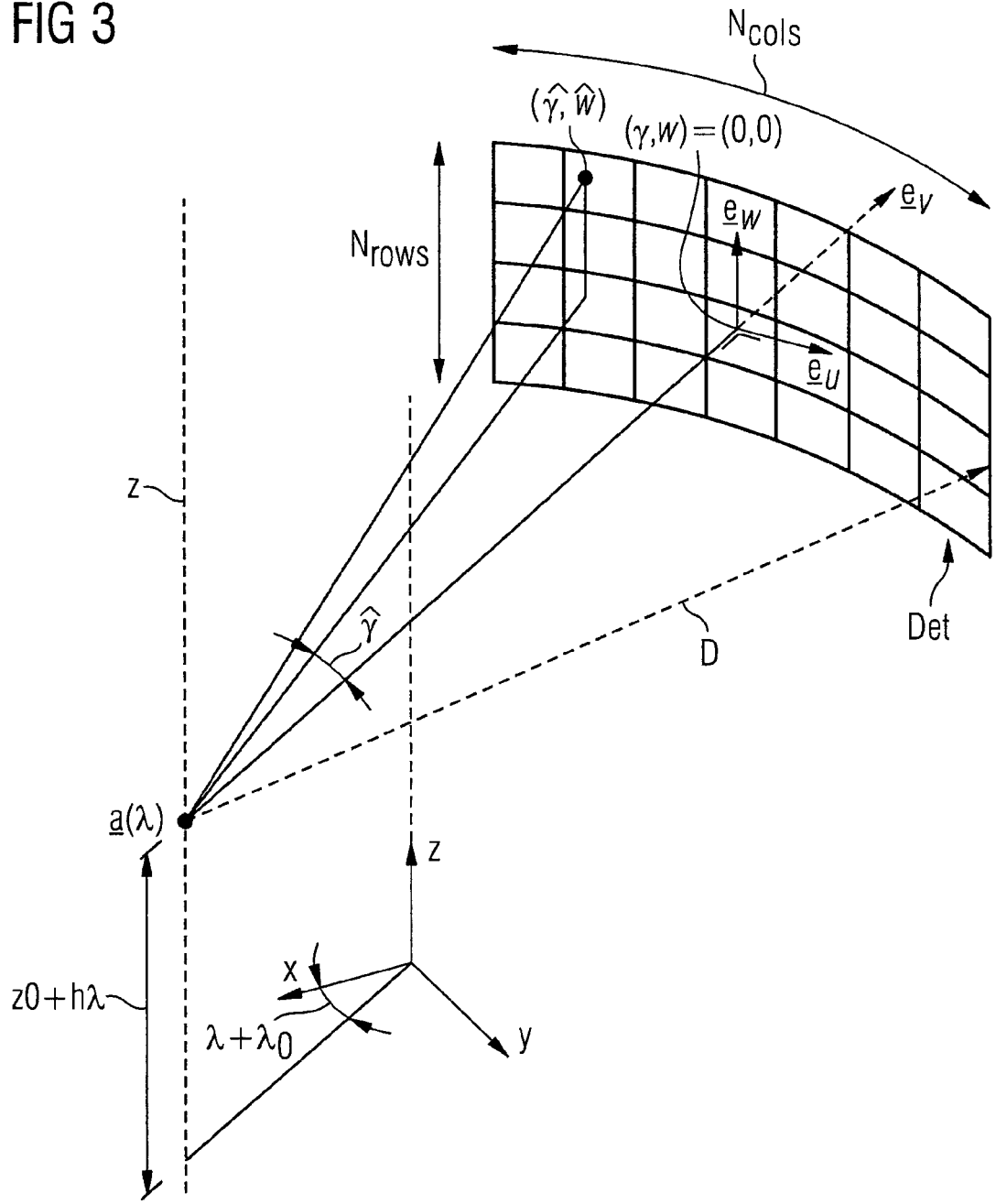
FIG. 3 A schematic representation of the geometry for the data acquisition.
Figure 4A:
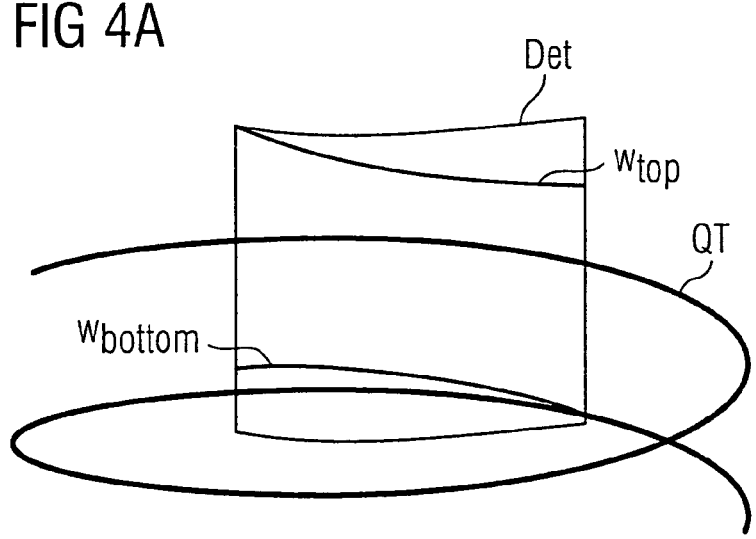
FIG. 4 Two schematic representations of a TD window on a detector.
Figure 4B:
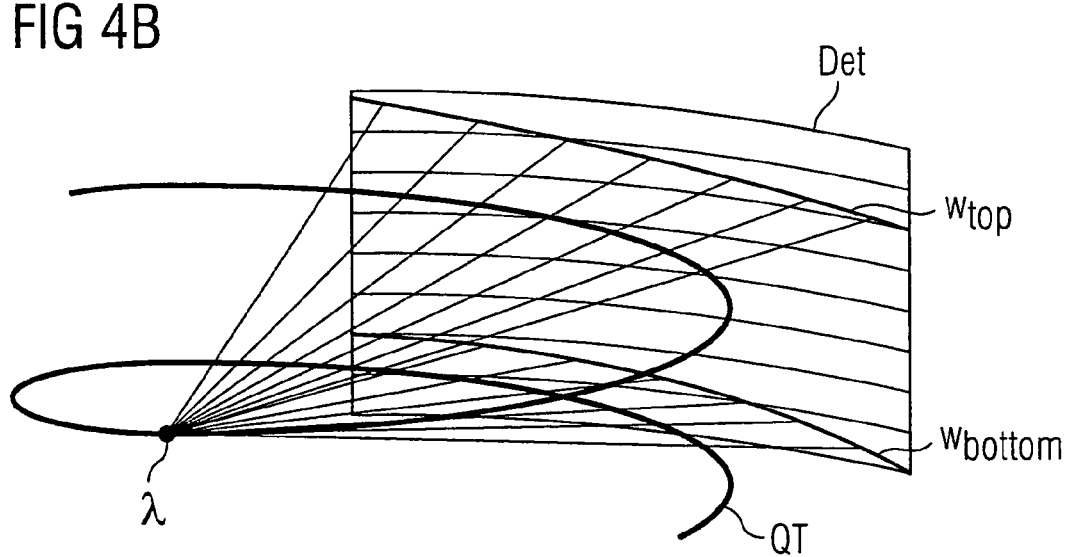

FIG. 4A shows the position of the TD window on the surface of the detector Det., wherein QT refers to the spiral path along which the X-ray source moves relative to the examined object. In contrast to FIG. 3 and to provide a clearer overall view, the limits between the individual detector pixels are not drawn in. The upper limit wtop and the lower limit wbottom of the TD window are drawn in as lines on the detector surface. The TD window corresponds to the surface between these lines. As shown in FIG. 4B, the TD window is obtained by imaging the projection of the X-ray source trajectory QT on the detector Det. Thus, if one sits on a specific point along the spiral path QT, the point λ in FIG. 4B, and if one projects the opposite-arranged section of the spiral path QT onto the detector Det, then the projection of the spiral path QT segment above the actual position λ represents the upper limit wtop and the projection of the spiral path QT segment below the actual position represents the lower limit wbottom of the TD window. The rays which start in FIG. 4B at the point λ pass through the opposite-arranged side of the spiral path QT, so that their points of incidence on the detector Det represent the searched-for projections and thus fall onto the upper limit wtop and the lower limit wbottom of the TD window.

The importance of the TD window is described, for example, in C. Bontus, T. Köhler "Reconstruction Algorithms for Computed Tomography," Advances in Imaging and Electron Physics, Vo. 151, Elsevier 2008, the entire contents of which are hereby incorporated herein by reference.

Prior to realizing a back projection of the CT data, a so-called "rebinning" is advantageously carried out in a pseudo-parallel "wedge" geometry. This method is described in further detail in K. Stierstorfer, A. Rauscher, J. Boese, H. Bruder, S. Schaller and T. Flohr: "Weighted FBP—a simple approximate 3D FBP algorithm for multislice spiral CT with good dose usage for arbitrary pitch." Phys. Med. Biol., Vol. 49, pp 2209-2218, 2004 for example, as well as in D. Heuscher, K. Brown and F. Noo: "Redundant data and exact helical cone-beam reconstruction." Phys. Med. Biol., Vol. 49, pp 2219-2238, the entire contents of each of which are hereby incorporated herein by reference.

This rebinning process can be expressed mathematically as follows:

$$gr(\varsigma(\lambda,\gamma), sr(\lambda,\gamma), w) = g(\lambda,\gamma,w), \tag{8}$$

with the rebinning equations $$\varsigma(\lambda, \gamma) = \lambda + \frac{\pi}{2} - \gamma, \; sr(\lambda, \gamma) = R0\sin\gamma \tag{9}$$

wherein the variable w remains unchanged.

With a rebinning of this type, which in the final analysis corresponds to a resorting of the measuring data, measuring data are usefully interpolated between the actual, real data measured at the detector Det, so as to generate a pseudo X-ray beam which has the desired geometry. A geometry arranged in this way allows describing the upper and the lower limits of the TD window as shown with the following equation (7):

$$wtop = \frac{Dh\pi/2 - \arcsin(s_r/R_o)}{R_o\sqrt{1 - s_r^2/R_o^2}}, \tag{10}$$

$$wbottom = \frac{Dh\pi/2 + \arcsin(s_r/R_o)}{R_o\sqrt{1 - s_r^2/R_o^2}}$$

The process steps described in the following can be used either with or without the rebinning.

An algorithm is described which allows realizing a precise reconstruction. For this, we initially proceed on the assumption—negated later on—that for each voxel of the volume of interest, data are detected continuously across a projection angle range of at least 180°. (This corresponds to the assumption, explained further later on, that exclusively uninterrupted data are detected for each voxel of the volume of interest, meaning that the projection of each voxel of the volume of interest enters and exits the detector only once, so that all existing data are measured "as one piece.")

Figure 5:
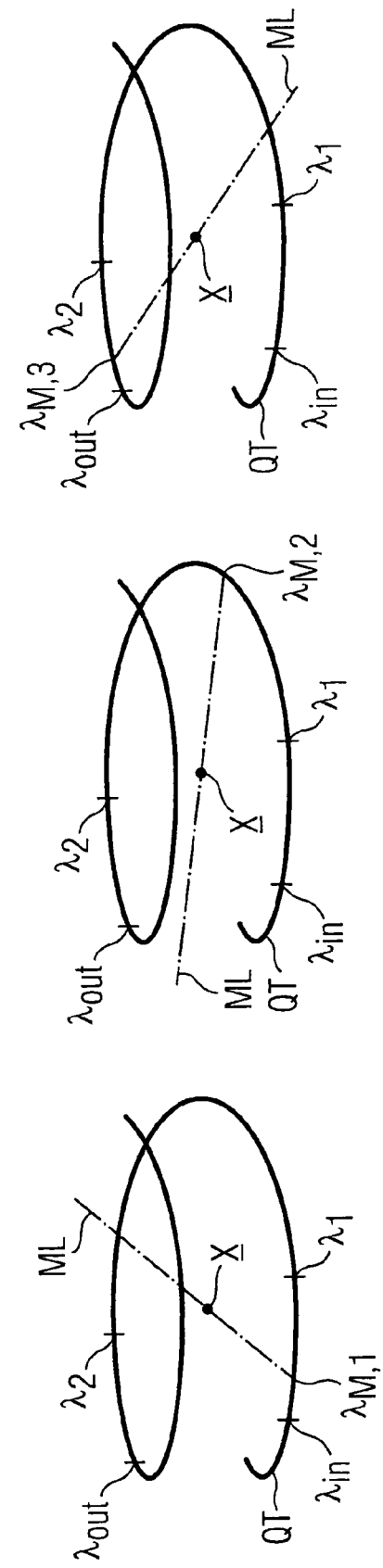
FIG. 5 Another schematic representation of three different M lines, which intersect a specific voxel at the x position, as well as the associated back projection regions on the X-ray source trajectory.

The spiral path QT of the X-ray source is shown three times in FIG. 5. The end points of the uninterrupted illumination are shown with λin and λout for three different cases, wherein this illumination respectively extends over a projection angle range of at least 180°. The voxel x of the volume of interest is thus irradiated continuously with X rays from the X-ray source position λin along the spiral path QT, up to the X-ray source position λout, wherein these X rays impinge on the detector Det. That is to say, all projections for the voxel x for the complete region impinge on the detector Det.

The X-ray source positions where the data detected with respect to the voxel x of the volume of interest enter the TD window are given the reference λ1 while the positions where the data detected with reference to the voxel x exit from the TD window are given the reference λ2. It can be seen that data are recorded above the region extending between λ1 and λ2, which corresponds to the data outside of the TD window. In the following, it is described how a mathematically precise reconstruction can be realized, which additionally uses data detected outside of the TD window. The use of these data is desirable since the image noise can be reduced in this way, meaning a better image can be obtained with the same dose.

A differentiated back projection on M lines is realized, wherein the M line is a line that connects an X-ray source position with an optional point on the detector Det. To explain the concept of the differentiated back projection (DBP) on M lines, the designation DBP {λa, λb, x} is used in the following for the differentiated back projection of the voxel x via the interval [λa, λb]. That is to say, for the back projection designated in this way data are used which are obtained in the region between the X-ray source positions λa and λb.

Since the above-described rebinning step, carried out prior to the back projection, results in a significant improvement with respect to efficiency and noise behavior, this differentiated back projection is preferably carried out with the rebinned geometry defined according to the equation (8). Analog to the above terms, the differentiated back projection of the rebinned measuring values gr (ς, sr, w) via the interval [ςa, ςb] on the voxel x for this geometry is referred to as DBPr {ςa1, ςb1, x}.

The back projection equation thus reads as follows:

$$DBPr\{\varsigma a1, \varsigma b1, x\} = \int_{\theta a}^{\theta b} g_d(\varsigma, sr*(\varsigma, x), w*(\varsigma, w))d\varsigma \tag{11}$$

wherein:

$$gd(\varsigma, sr, w) = \frac{D}{\sqrt{D^2 + w^2}} \frac{\partial}{\partial s_r} gr(\varsigma, sr, w) \tag{12}$$

$$sr*(\varsigma, x) = x\cos(\varsigma + \varsigma o) + y\sin(\varsigma + \varsigma o) \text{ and} \tag{13}$$

$$w*(\varsigma, x) = \frac{D(z - z_0 - h(\vartheta - \pi/2 + \arcsin(s_r^*/R_o)))}{y\cos(\vartheta + \vartheta_o) - x\sin(\vartheta + \vartheta_o) + \sqrt{R_o^2 - s_r^{*2}}} \tag{14}$$

Mathematically, the two variants of the differentiated back projection (without rebinning and with rebinning) are connected by the equation $$DBP\{\lambda a, \lambda b, x\} = DBPr\{\varsigma^*(\lambda a, x), \varsigma^*(\lambda b, x), x\} \tag{15}$$

with the equation $$\varsigma*(\lambda a, x) = \lambda + \frac{\pi}{2} - \gamma*(\lambda, x) \tag{16}$$

(see equation (9)) and $$\gamma*(\lambda, x) = \arctan\left(\frac{y\cos(\lambda + \lambda_o) - x\sin(\lambda + \lambda_o)}{R_o - x\cos(\lambda + \lambda_o) - y\sin(\lambda + \lambda_o)}\right) \tag{17}$$

Independent of which variant of the differentiated back projection is used, meaning whether or not a rebinning is first carried out, the back projection does not result in the searched-for object itself (meaning the weakening value f(x) of the respectively reconstructed voxel) but its Hilbert transform along a specified line, which in the present case is along the above-defined M line. An inverse Hilbert transformation must therefore be carried out after the back projection. Since we must proceed on the assumption that the searched for function f(x) is defined only over a limited range, a finite inverse Hilbert transformation can be realized without problem.

The precise procedural steps required for realizing the inverse Hilbert transformation are described in the article by H. Schondube, K. Stiersdorfer, F. Dennerlein, T. White and F. Noo: "Towards an efficient two-step hilbert algorithm for helical cone-beam CT." in Proc. 2007 Meeting on Fully 3D Image Reconstruction in Radiology and Nuclear Medicine (Lindau, Germany), F. Beckman and M. Kachelriess, Eds., 2007, pp 120-123 (the entire contents of which are hereby incorporated herein by reference) in which a differentiated back projection is also explained, but for n lines. The method described therein for the back projection of n lines and the subsequent inverse Hilbert transformation can be used analog in a correspondingly changed manner also for the back projection of M lines since the n lines form a sub group of the M lines, so that we point to the aforementioned document with respect to the mathematical details.

In the following, the Hilbert transform of a desired weakening value f(x) at the location of a voxel x along the unit vector to is given the designation (Hf)(x, ω) and the unit vector from the point a(λ) from the x-ray source spiral in the direction x is given the designation ω (λ, x). With this notation, a back projection onto M lines (the M line corresponds in this case to a line along the unit vector ω) can be expressed as follows:

$$(Hf)(x, \omega(\lambda M, x)) = \frac{1}{2}(DBP\{\lambda M, \lambda 2, x\} + DBP\{\lambda M, \lambda 1, x\}) \quad (18)$$

The same is true for each voxel x within the helix, as long as x was irradiated uninterrupted in the intervals between λM and λ2 and between λM and λ1.

The line ML (see FIG. 5), which connects the source position a(λM) with x, defines the direction of the Hilbert transform, meaning the result of the back projection depends on λM. Only after realizing the inverse Hilbert transformation is the result of the reconstruction mathematically independent of the selection of λM, wherein it is not necessary for λM to be positioned in the interval between λ1 and λ2 that delimits the TD window. It is only necessary that λM is positioned such that the aforementioned uninterrupted illumination is present. The limits for this region of uninterrupted illumination are set by λin and λout. The option of selecting λM independent of the TD window shows that it is possible to take into account redundant measuring data from outside of the TD window for the reconstruction.

FIG. 5 shows three different starting points λM,1, λM,2, λM,3 for three different M lines. The segment of the source trajectory QT that is bolded in this case marks the source positions which contribute to a back projection according to the equation (18). In the case shown on the left side (λM=λM, 1<λ1) the complete back projection interval extends from λM=λM,1 to λ2. If λM is between λ1 and λ2 (center case with λM,2), then the back projection interval extends from λ1 to λ2. In the third case (right side), λM=λM,3>λ2, so that the back projection is carried out over all λ from λ1 to λM, 3. In the center case, only data from the TD window are used for the back projection. In the left case, redundant data below the TD window are also used and in the right case, redundant data from above the TD window are used for the back projection.

However, a back projection of this type for individual voxels is not efficient. A volume-based reconstruction is therefore realized by processing a whole group of parallel M lines simultaneously. For this, the desired volume V to be totally reconstructed is divided into a stack of surfaces, which are respectively formed by a group of M lines, arranged parallel to each other in pairs.

Figure 6:
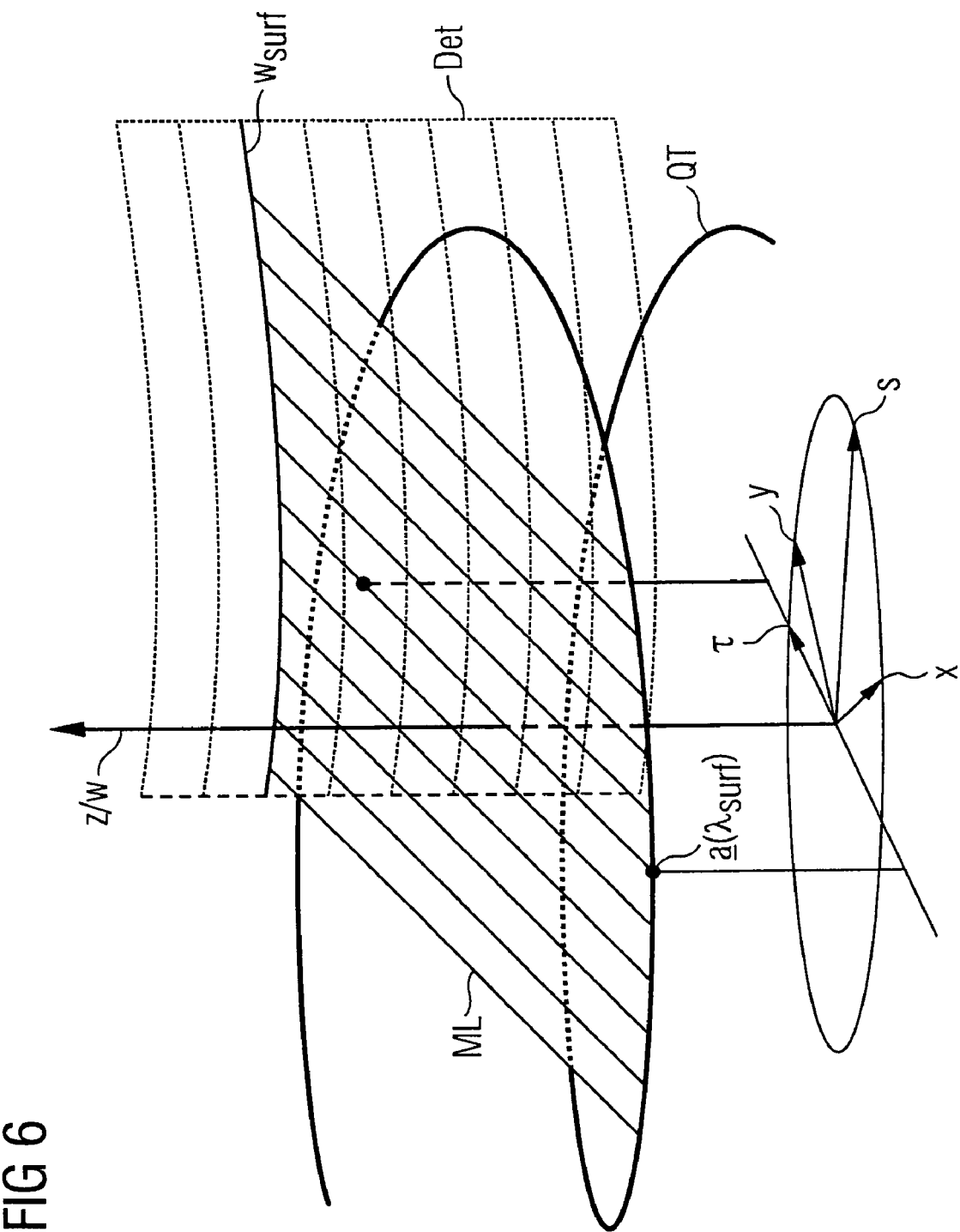
FIG. 6 A surface formed by M lines, shown schematically with reference to the X-ray source trajectory and the TD window on the detector surface.

FIG. 6 shows an M line surface that is spanned by a plurality of parallel M lines ML. Each of the M lines ML impinge on the detector Det in the same detector line wsurf. The different lines of the detector Det are separated in FIG. 6 by dotted lines. The M lines ML of the M line surface are equidistant and parallel to each other if they are projected onto the x-y plain. Precisely one M line ML that intersects the z axis exists for a specific M line surface. The λ value of this M line is given the reference λsurf. By varying λsurf from −∞ to +∞ (or also a narrower range) with constant wsurf, we obtain a stack of disks which cover the complete volume of interest. A detector line called wsurf is therefore selected first, and subsequently an image reconstruction is realized for all M line surfaces resulting from a variation of λ. In this way, the complete volume of interest is reconstructed.

This process is followed not only for a detector line and thus for a single wsurf, but also for several detector lines. A representation of M line surfaces for different wsurf can be found in FIG. 7. This Figure shows three variants, wherein respectively the source trajectory QT, the detector surface Det, as well as the Tam-Danielsson window TD formed thereon through the projection of the source trajectory QT are shown in the drawing with the aid of the upper limit wtop and the lower limit wbottom. Each of the three M line surfaces is therefore characterized by a detector line wsurf where the respective surface intersects with the detector Det, as well as the direction of the M lines ML, which are indicated by the position λsurf on the source trajectory QT. This relates to the central M line ML, which intersects with the z axis.

As described in the above, the values for λ can be varied for a specific wsurf in order to display the total volume of interest with a group of M lines. This is done for each of the three detector lines wsurf shown in FIG. 7. Three groups of M line surfaces therefore exist—wherein only one M line surface of each group is shown in FIG. 7—which can respectively be used for the reconstruction of an image of the volume of interest.

Figure 7:
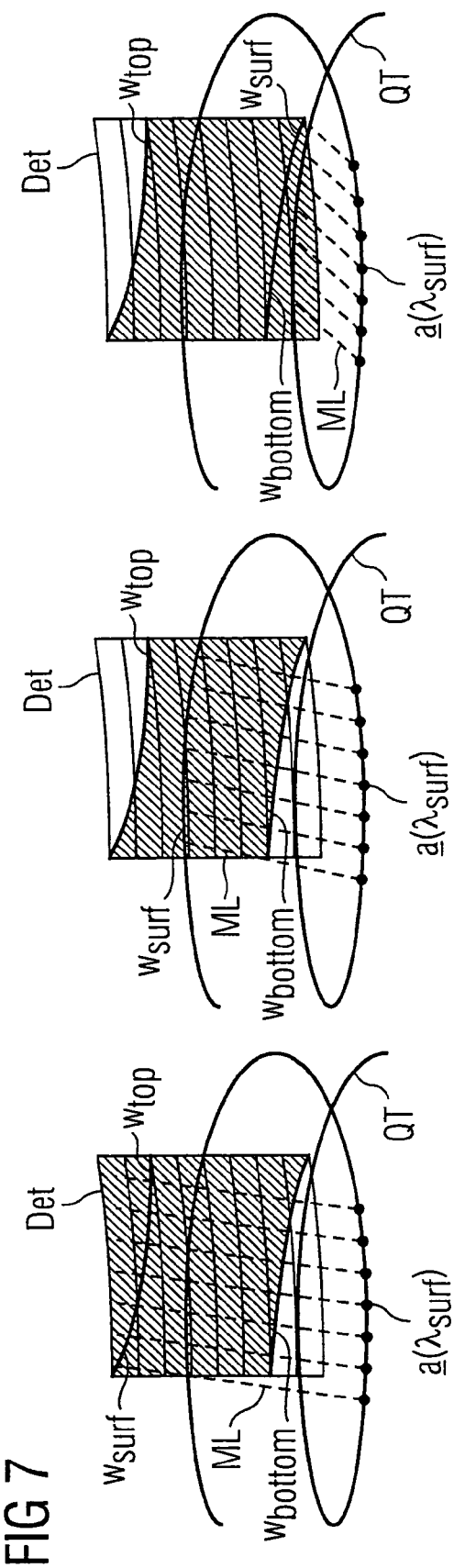
FIG. 7 Three different M line surfaces.

A case is illustrated in the center of FIG. 7, for which the surface formed by the M lines ML intersect the detector Det at a detector line wsurf that is located completely inside the TD window. The detector line wsurf for the case shown on the left side is located above the TD window, meaning precisely at the upper edge of the detector Det on the uppermost detector line. The reverse case is shown on the right-hand side, for which the M lines ML are selected such that the surface formed therewith falls onto the lower edge of the detector Det, meaning onto the lowest detector line wsurf and thus is located below the TD window. The hatched area therefore shows the respective detector region from which measuring data are taken into consideration during a volume-based back projection. It is easy to see that redundant data from a region above the TD window are used in the case shown on the left, that data only from the TD window are used in the center case, and that redundant data from a detector region below the TD window are used for the right-hand case. If we compare this to the representation in FIG. 5, then the case shown in the center of FIG. 7 corresponds to the case shown in the center of FIG. 5, the case shown on the left in FIG. 7 corresponds to the case shown on the left in FIG. 5 and the case shown on the right in FIG. 7 corresponds to the case on the right in FIG. 5.

It is particularly advantageous to select the three surfaces in the same way as shown schematically in FIG. 7, meaning back projections of the volume are carried out via three different stacks of surfaces, wherein a first stack of surfaces is selected such that each surface directly adjoins the lower edge of the detector Det. For the second back projection and/or reconstruction, a stack of surfaces is selected for which the surfaces are located precisely in the TD window and for the third back projection, a stack of surfaces is selected for which the surfaces are located above the TD window, at the upper edge of the detector Det. It is thus ensured that a high number of redundant data are used and that the detector Det is therefore utilized to the highest possible degree.

For the back projection, the individual voxels on the surfaces defined by the M lines are defined with an ortho-normal grid $(s, \tau)$ (see FIG. 6), which rotates with the direction of the M lines along the source trajectory QT. The coordinates s and $\tau$ are measured along the following orthogonal axes:

$$es(\lambda surf) = |-\sin(\lambda surf+\lambda o), \cos(\lambda surf+\lambda o), 0| \quad (19)$$

$$es(\lambda surf) = |-\cos(\lambda surf+\lambda o), -\sin(\lambda surf+\lambda o), 0| \quad (20)$$

In other words, the projections of the M lines on the x/y plane are parallel lines to the unit vector $e\tau$. These lines are at a distance s to the origin and are given mathematical signs, wherein s positive is measured in the direction of es and $\tau$ represents a coordinate along the projection of the M line onto the x/y plane. The Cartesian position of a point $(s, \tau)$ onto a M line surface is expressed as:

$$x = -s \sin(\lambda surf + \lambda o) - \tau \cos(\lambda surf + \lambda o) \quad (21)$$

$$y = -s \cos(\lambda surf + \lambda o) - \tau \sin(\lambda surf + \lambda o) \quad (22)$$

$$z = zo + h\left(\lambda_{surf} + \arcsin\left(\frac{s}{R_o}\right)\right) + \frac{\tau + \sqrt{R_o^2 - s^2}}{D_R} \cdot w_{surf} \quad (23)$$

For a reconstruction of the desired volume V(x) on a Cartesian grid of voxels of the size $(\Delta x, \Delta y, \Delta z)$, a constant value is initially assumed for wsurf and subsequently a range of $\lambda$surf values computed, which are necessary to cover the complete volume V with M line surfaces. Following this, the M line surfaces within this region are formed, wherein the distance between them is $$\Delta \lambda surf = \Delta z/h \quad (24)$$

The back projection is then carried out on these surfaces by using the equation (18), followed by the inverse Hilbert transformation.

This is followed by a conversion to Cartesian coordinates using a two-step interpolation. First, an interpolation is realized from the $(s, \tau, \lambda surf)$ grid to an intermediate coordinate system $(x, y, \lambda surf)$, using the equations (21) and (22), which is then followed by a conversion and/or an interpolation into the Cartesian grid with the aid of the equation (23).

This reconstruction of the same volume is realized three times, meaning with three different groups of M line surfaces (once with surfaces within the TD window, as shown on the left in FIG. 7, once with surfaces in the center of the TD window as shown in the center of FIG. 7 and once with surfaces above the Tam-Danielsson window as shown on the right in FIG. 7). As a result, three volume images f1(x), f2(x), f3(x) are reconstructed, which are then averaged with the aid of $$\tilde{f}(x) = \frac{f_1(x) + f_2(x) + f_3(x)}{3} \quad (25)$$

in order to carry out the final reconstruction $\tilde{f}(x)$ of the volume of interest.

According to the equation (25), the weakening value $\tilde{f}(x)$ for each individual voxel at the location x is obtained by averaging the three reconstructions, meaning an average weakening value is formed. The desired weakening distribution $\tilde{f}(x)$ of the volume V(x) to be reconstructed is formed in this way. Of course, such an average can also be obtained by weighting. For example, the reconstruction from the data stemming only from the TD window can be weighted more than that of the reconstructions which also contain the redundant data, wherein a different joint processing of the three volume images f1(x), f2(x), f3(x) into a final image $\tilde{f}(x)$ is also possible.

A reconstruction method is thus made available, which is mathematically exact and also prevents the occurrence of artifacts that could result from the cone shape of the X-ray radiation, even for detectors having numerous detector lines. The use of the redundant data furthermore results in a considerable reduction of the image noise, thus allowing the full use of the applied dose. The noise reduction is the result of the averaging according to the equation (25).

The assumption was initially made that the voxel x was illuminated without interruption, so that complete measuring data from a projection angle of more than 180° are available. However, that is not the case for the interrupted illumination. The expression "interrupted illumination" describes the situation where the voxel x is illuminated only in disjunctive regions without interruption over a projection angle range exceeding 180°. The projection of the voxel thus enters the detector region at a specific $\lambda$ value for the X-ray source trajectory, exits from this region at a later $\lambda$ value and then enters this detection region once more.

Figure 8:
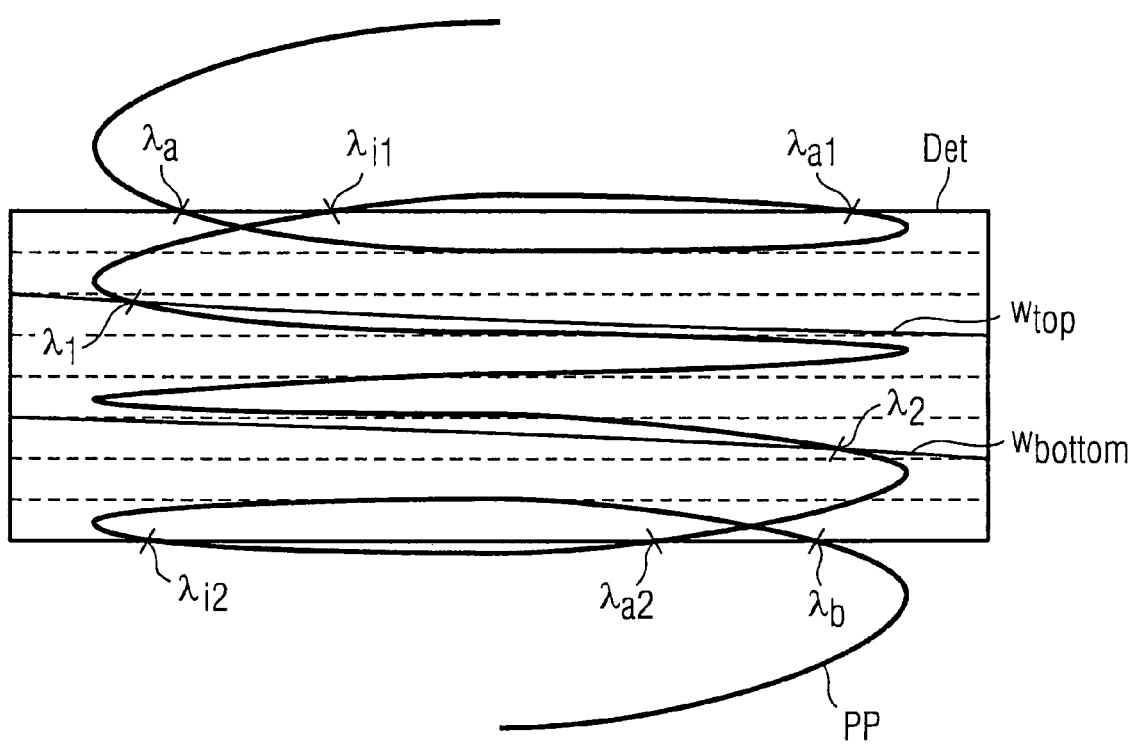
FIG. 8 A view designed to illustrate the interrupted illumination.

The interrupted illumination is shown schematically in FIG. 8, which shows the detector Det and the TD window located between the lower limit wbottom and the upper limit wtop. The different lines of the detector Det are separated from each other by dotted lines. The curve PP represents the projection of the voxel x on the detector Det. This projection PP is obtained by connecting the actual position of the X-ray source with the location x of the voxel and by determining the location where this connecting line meets the detector Det. The projection PP thus does not correspond to the X-ray source trajectory QT of the other Figures.

The projection of the voxel x for the first time enters the detector Det at the X-ray source position $\lambda a$. Starting with this point in time, data for the voxel x are detected. The projection falls again outside of the detector Det between the X-ray source positions $\lambda o1$ and $\lambda i1$, which corresponds to an interval of the interrupted illumination. Starting with the X-ray source positions $\lambda i1$, the projection PP again falls within the detector Det and the TD window is reached at the X-ray source positions $\lambda 1$. The projection leaves the TD window again at the X-ray source position $\lambda 2$. A second interval of the interrupted illumination is located between the X-ray source positions $\lambda o2$ and $\lambda i2$, before the projection PP finally leaves the detector Det completely at the X-ray source position $\lambda b$.

Whether or not an interrupted illumination occurs depends on the selection of the pitch factor, which is defined as $$p = 2\pi h \frac{D}{R_o N_{rows} \Delta w} \quad (26)$$

with $2\pi h$ representing the pitch height of the helical path, D representing the distance between the X-ray source and the detector Det, Nrows representing the number of detector lines and $\Delta w$ the expansion of each detector line. Thus, the pitch factor shows how many times relative to a detector width the X-ray source moves in the direction z during each rotation.

Pitch factor values exist for which a continuous illumination occurs between X-ray source positions $\lambda a$ and $\lambda b$, meaning at these pitch values no intervals of interrupted illumination occur, in contrast to the representation shown in FIG. 8. These pitch values are between the two limit pitch values pmin and pmax, wherein $$p\min = \pi \frac{N_{rows} - 1}{N_{rows}} \sin(\gamma\max) \text{ and} \quad (27)$$

$$p\max = \pi \frac{N_{rows} - 1\cos(\gamma_{max})}{N_{rows}\pi/2 + \gamma_{max}}$$

For this case, $\gamma$max stands for the highest possible value for $\gamma$ (see FIG. 3 concerning the geometry). The initial assumption that no uninterrupted illumination occurs corresponds to the assumption that the CT data are detected at pitch values within the limits between pmin and pmax. In the following, we consider the situation where the pitch is below the value for this area, thereby resulting in the interrupted illumination shown in FIG. 8. The effect of the interrupted illumination increases with a decrease in the pitch.

For pitch values above pmax the TD window in part is located outside of the detector Det range. Raw data over a projection angle range of at least 180° are consequently not available for all voxels and a stable mathematically precise reconstruction is not possible. These large pitch values are therefore not taken into consideration in the following.

An interruption in the illumination therefore cannot occur in the interval between the X-ray source positions $\lambda 1$ and $\lambda 2$. As a result of geometric considerations and definitions of the TD window, it can be shown that—independent of the pitch—the projection PP of an optional voxel enters the TD window precisely once and/or leaves this window precisely once. Since the TD window is located completely within the detector limits, the projection PP cannot leave the detector as long as it is located inside the TD window. (For this, see also: H. Schondube, K. Stierstorfer, F. Noo: "Accurate helical CT reconstruction with redundant data," Physics in Medicine and Biology, 2009, the entire contents of which are hereby incorporated herein by reference).

This aspect is important for the use of the content described with respect to the FIG. 7 and the maximum pitch: for the case in the center of FIG. 7, only data from the TD window are used. The reconstruction for wsurf within the TD window is therefore not a problem for a CT scan with interrupted illumination. Since the interrupted illumination does not relate to the TD window, continuous data are available which can be used for the reconstruction. The image reconstruction f1 can therefore take place without modification even if the illumination is interrupted, as described in the above.

However, the situation is different for the left and the right case in FIG. 7. In that case, the detector lines wsurf were selected such that they are located outside of the TD window. FIG. 8 shows that interrupted illumination can occur within these data. It means that for the image reconstructions f2 and f3, measuring data is not available for all projection angles relating to the voxel x, which can be used for the reconstruction.

To be able to realize an image reconstruction for the left case in FIG. 7, corresponding to f2, and for the right case in FIG. 7, corresponding to f3, the missing data are compensated in the regions where the illumination is interrupted. For the left case in FIG. 7, these are the data between the X-ray source positions $\lambda o1$ and $\lambda i1$ (see FIG. 8) and for the right case in FIG. 7, these are the data between the X-ray source positions $\lambda o2$ and $\lambda i2$ (see FIG. 8). For this compensation, three options are introduced as examples.

First of all, it is possible to replace the data missing as a result of the interrupted illumination with the data of the upper (for the left case in FIG. 7) and/or the lower (for the right case in FIG. 7) detector line, which so-to-speak corresponds to a never-ending continuation of the detector Det toward the top and/or the bottom. The physically non-existing lines are filled in with data from the nearest physically existing lines. The same is true, of course, for the deviation where as alternative to FIG. 7 other detector lines are used as wsurf in the left and the right case in place of the topmost and/or the lowest detector line.

A second option is to determine measuring data from the computed image f1 through a forward projection. This also corresponds to a never-ending continuation of the detector toward the top and the bottom, but the data of the physically non-existing lines are obtained from the computed reconstruction f1. However, this requires on the one hand a forward projection step for computing the missing measuring data, which is followed by a second back projection step for computing the reconstructions f2 and f3 from the measured as well as the compensated measuring data.

The third option also makes use of the already computed image f1. Valid is therefore the relation between the differentiated back projection (DBP) and the Hilbert transform (see also the publication by J. Pack, F. Noo and R. Clackdoyle: "Cone-beam reconstruction using the backprojection of locally filtered projections," IEEE Trans. Med. Imag., Vol. 24, No. 1, pp. 70-85, January 2005, the entire contents of which are hereby incorporated herein by reference), which has already been introduced as equation (18) in the above.

$$(Hf)(x, \lambda M) = \frac{1}{2}(DBP\{\lambda M, \lambda 2, x\} + DBP\{\lambda M, \lambda 1, x\}) \quad (18)$$

The equation (18) is considered for the case that the M lines point to the upper end of the detector Det (left case in FIG. 7), so that interrupted illumination occurs, meaning $\lambda M = \lambda o < \lambda 1$. According to FIG. 8, $\lambda o1$ and $\lambda i1$ represent the starting and ending points of the interval for the interrupted illumination. Each of the two terms on the right side of the equation (18) can be rewritten as the sum of three terms:

$$DBP\{\lambda M, \lambda 2, x\} = DBP\{\lambda M, \lambda o1, x\} + DPB\{\lambda o1, \lambda i1, x\} + DBP\{\lambda i1, \lambda 2, x\} \quad (28)$$

$$DBP\{\lambda M, \lambda 1, x\} = DBP\{\lambda M, \lambda o1, x\} + DPB\{\lambda o1, \lambda i1, x\} + DBP\{\lambda i1, \lambda 1, x\} \quad (29)$$

In the process, the first and the third term on the right side of the equations (28) and (29) can be computed directly from the existing measuring data. However, that is not the case for the center term, which relates only to the interval of the interrupted illumination.

The following furthermore applies (see the publication by J. Pack, F. Noo and R. Clackdoyle: "Cone-beam reconstruction using the backprojection of locally filtered projections," IEEE Trans. Med. Imag., Vol. 24, No. 1, pp. 70-85, January 2005, the entire contents of which are hereby incorporated herein by reference):

$$DBP\{\lambda1, \lambda o, x\} = (Hf)(x, \lambda o) - (Hf)(x, \lambda 1) \tag{30}$$

If we insert the two equations (28) and (29) into the equation (18) and use the relation according to the equation (30) for the second term on the right side of the equations (28) and (29), meaning we insert the inverse Hilbert transformation in place of the differentiated back projection, we obtain the following:

$$(Hf)(x, \omega(\lambda M, x)) - (Hf)(x, \lambda i1) + (Hf))(x, \lambda o1) = \tag{31}$$
$$\frac{1}{2}(DBP\{\lambda M, \lambda o1, x\} + DBP\{\lambda i1, \lambda 2, x\} +$$
$$DBP\{\lambda M, \lambda o1, x\} + DBP\{\lambda i1, \lambda 1, x\})$$

On the left side of the equation (31) are two unknown variables: (Hf)(x, λi1) and (Hf)(x,λo1). These two variables can be obtained directly from the already computed image f1. The values from the reconstructed volume f1 along the M lines are used or interpolated, which point from the source point λdi and/or from the source point λi2 in the direction of the voxel x. Following this, respectively one forward Hilbert transformation is realized along these lines. The two missing variables (Hf)(x, λi1) and (Hf)(x, λo1) are the result of this Hilbert transformation.

The four expressions on the right side of the equation (31) can be computed directly from the measured data. As can be seen with the aid of FIG. 8, measuring data are available continuously and without interruption for the relevant intervals [λM, λ01], [λi1, λ2], [λi1, λ1] (see above: λM=λa).

As a result, it is possible to compute the inverse Hilbert transformation of the four terms on the right side of the equation (31) and the term (Hf)(x, λi1)−(Hf)(x, λ01) obtained from the image f1, thereby arriving at the image f2.

The last-described, third option for supplementing the measuring data missing because of the interrupted illumination is preferred over the second option since the first-named option only requires the computation of the two Hilbert transforms (Hf)(x, λi1) and (Hf)(x, λo1) from the image f1. Of course the two interval ends λo1 and λi1 must first be determined, which depend on the location x of the voxel that is being considered.

In an analog manner to the image f2, the image f3 for the case on the right side of FIG. 7 can be computed using the previously computed image f1, meaning for λM=λb. In place of the equation (31), we then obtain the following equation:

$$(Hf)(x, \omega(\lambda M, x)) - (Hf)(x, \lambda i2) + (Hf))(x, \lambda o2) = \tag{32}$$
$$\frac{1}{2}(DBP\{\lambda M, \lambda o2, x\} + DBP\{\lambda i2, \lambda 2, x\} +$$
$$DBP\{\lambda M, \lambda o2, x\} + DBP\{\lambda i2, \lambda 1, x\})$$

As a result of this compensation for the interrupted illumination—alternatively according to one of the above-described three methods—complete data for the mathematically precise reconstruction are now also available for the left and the right case in FIG. 7. The effect of the interrupted illumination has thus been eliminated. As described in the above, an image reconstruction for f2 and f3 can be realized with the aid of a differentiated back projection and an inverse Hilbert transformation, which makes it possible to compute an improved image f(x) from f1, f2 and f3 through averaging.

A method has been presented herein, which permits a precise reconstruction of spiral CT data by also using the redundant data from outside of the TD window while permitting a freely selectable pitch. This method in particular solves the problem of the interrupted illumination occurring with the spiral CT scan.

The invention has been described in the above with an exemplary embodiment. It is understood that numerous changes and modifications are possible without leaving the actual scope of the invention. In particular, four or more image reconstructions can be used in place of the three image reconstructions to compute a final image.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. Method for reconstructing image data of an examined object by using measuring data, wherein the measuring data for a relative spiral movement between a radiation source of a computer tomography system and the examined object are detected by a detector within and outside of its Tam-Danielsson window, wherein based on the spiral movement the measuring data from outside of the Tam-Danielsson window is present with at least one interruption, the method comprising:
    realizing a mathematically precise first reconstruction of first image data by using only the measuring data from the Tam-Danielsson window;
    realizing a mathematically precise second reconstruction of second image data by using at least measuring data outside of the Tam-Danielsson window, wherein the at least one interruption in the measuring data is compensated for by using at least one of available measuring data, the first image data and other image data that were reconstructed from available measuring data; and
    combining the first image data and the second image data.

2. Method according to claim 1, wherein available measuring data are used for the compensation by interpolating or extrapolating available measuring data onto the at least one interruption, upon which the mathematically precise second reconstruction is based.

3. Method according to claim 2, wherein a mathematically precise third reconstruction of third image data is realized by using at least among other things measuring data from outside of the Tam-Danielsson window, wherein the at least one interruption of the measuring data is compensated for by using at least one of available measuring data and the first image data, and wherein the first image data and the second image data and the third image data are then combined.

4. Method according to claim 2, wherein the image data are combined with the aid of an averaging.

5. Method according to claim 1, wherein the first image data are used for the compensation by computing from the first image data projection data that correspond to the at least one interruption, wherein these are subsequently used for the mathematically precise second reconstruction.

6. Method according to claim 5, wherein a mathematically precise third reconstruction of third image data is realized by using at least among other things measuring data from outside of the Tam-Danielsson window, wherein the at least one interruption of the measuring data is compensated for by using at least one of available measuring data and the first image data, and wherein the first image data and the second image data and the third image data are then combined.

7. Method according to claim 5, wherein the image data are combined with the aid of an averaging.

8. Method according to claim 1, wherein the first image data are used for the compensation by computing Hilbert transformations from the first image data, upon which the mathematically precise second reconstruction is based.

9. Method according to claim 8, wherein a mathematically precise third reconstruction of third image data is realized by using at least among other things measuring data from outside of the Tam-Danielsson window, wherein the at least one interruption of the measuring data is compensated for by using at least one of available measuring data and the first image data, and wherein the first image data and the second image data and the third image data are then combined.

10. Method according to claim 8, wherein the image data are combined with the aid of an averaging.

11. Method according to claim 1, wherein a mathematically precise third reconstruction of third image data is realized by using at least among other things measuring data from outside of the Tam-Danielsson window, wherein the at least one interruption of the measuring data is compensated for by using at least one of available measuring data and the first image data, and wherein the first image data and the second image data and the third image data are then combined.

12. Method according to claim 11, wherein the first and the second the third reconstruction are volume-based reconstructions with the aid of differentiated back projections and a following inverse Hilbert transformation.

13. Method according to claim 12, wherein the volume-based reconstruction for the first image data is realized with the aid of a differentiated back projection over a first group of surfaces formed by M lines, the volume-based reconstruction for the second image data is realized with the aid of differentiated back projections via a second group of surfaces formed by M lines and, the volume-based reconstruction for the third image data is realized with the aid of differentiated back projections over a third group of surfaces formed by M lines.

14. Method according to claim 13, wherein for the first group each of the respective surfaces formed by the M lines completely impinges on the detector within the Tam-Danielsson window, for the second group, each of the respective surfaces formed by the M lines impinges on the detector either above or below the Tam-Danielsson window and for the third group, each of the respective surfaces formed by the M lines impinges on the detector either above or below the Tam-Danielsson window.

15. Apparatus for reconstructing image data of an examined object by using measuring data, wherein the measuring data for a relative spiral movement between a radiation source of a computer tomography system and the examined object are detected by a detector within and outside of its Tam-Danielsson window, wherein based on the spiral movement the measuring data from outside of the Tam-Danielsson window is present with at least one interruption, the apparatus comprising:
means for realizing a mathematically precise first reconstruction of first image data by using only the measuring data from the Tam-Danielsson window;
means for realizing a mathematically precise second reconstruction of second image data by using at least measuring data outside of the Tam-Danielsson window, wherein the at least one interruption in the measuring data is compensated for by using at least one of available measuring data, the first image data and other image data that were reconstructed from available measuring data; and
means for combining the first image data and the second image data.

16. Method according to claim 1, wherein the image data are combined with the aid of an averaging.

17. Method according to claim 1, wherein the first and the second reconstruction are volume-based reconstructions with the aid of differentiated back projections and a following inverse Hilbert transformation.

18. Method according to claim 17, wherein the volume-based reconstruction for the first image data is realized with the aid of a differentiated back projection over a first group of surfaces formed by M lines, and the volume-based reconstruction for the second image data is realized with the aid of differentiated back projections via a second group of surfaces formed by M lines.

19. Method according to claim 18, wherein each group of surfaces covers the volume of interest of the examined object.

20. Method according to claim 18, wherein for the first group each of the respective surfaces formed by the M lines completely impinges on the detector within the Tam-Danielsson window, and for the second group, each of the respective surfaces formed by the M lines impinges on the detector either above or below the Tam-Danielsson window.

21. Method according to claim 18, wherein all M lines within one group impinge on the same detector line.

22. Method according to claim 18, wherein all M lines that form a surface are parallel when these are projected onto a plane that is perpendicular to the longitudinal axis of the spiral movement.

23. Method according to claim 18, wherein data are interpolated between the measuring data, so that the M lines of each surface are equidistant.

24. Method according to claim 18, wherein the reconstructed image data of the different reconstructions are transformed into Cartesian coordinates and the image data are combined within this coordinate system.

25. Method according to claim 1, wherein the spiral movement is determined such that the Tam-Danielsson window is relatively smaller than a dimension of the Tam-Danielsson window when it meets outside edges of two outermost ones of the detector lines.

26. A control and computer unit for reconstructing image data of an examined object, using measuring data from a computed tomography (CT) system, the control and computer unit comprising:
a processor; and
a memory storing program code, wherein the program code stored in the program memory, when executed on the processor, realizes the method according to claim 1.

27. A Computed Tomography (CT) system comprising:
a first radiation source and an oppositely positioned a first detector attached to a movable support allowing for scanning of a patient so as to obtain projection data from a plurality of projection angles;
a patient stretcher; and
the control and computer unit according to claim 26.

28. A Computed Tomography (CT) system comprising:
a first radiation source and an oppositely positioned a first detector attached to a movable support allowing for scanning of a patient so as to obtain projection data from a plurality of projection angles;
a patient stretcher; and
the apparatus according to claim 15.

29. A non-transitory computer readable medium including program segments for, when executed on a processor of a computer device, causes the computer device to implement the method of claim 1.

* * * * *